(12) United States Patent
Wilson et al.

(10) Patent No.: US 9,549,711 B2
(45) Date of Patent: *Jan. 24, 2017

(54) PATIENT SUPPORT PADS FOR USE IN DETECTING LYMPHEDEMA THROUGH X-RAY SCANS

(71) Applicant: Hologic, Inc., Bedford, MA (US)

(72) Inventors: Kevin Wilson, Acton, MA (US); Thomas L. Kelly, Woburn, MA (US)

(73) Assignee: HOLOGIC, INC., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,416

(22) Filed: Aug. 28, 2015

(65) Prior Publication Data

US 2015/0366520 A1    Dec. 24, 2015

Related U.S. Application Data

(63) Continuation of application No. 13/894,700, filed on May 15, 2013, now Pat. No. 9,119,542.

(60) Provisional application No. 61/648,742, filed on May 18, 2012.

(51) Int. Cl.
| | |
|---|---|
| *A61B 6/04* | (2006.01) |
| *G01N 23/06* | (2006.01) |
| *A61G 13/12* | (2006.01) |
| *A61B 6/00* | (2006.01) |

(52) U.S. Cl.
CPC ............. *A61B 6/5252* (2013.01); *A61B 6/04* (2013.01); *A61B 6/0421* (2013.01); *A61B 6/482* (2013.01); *A61B 6/505* (2013.01); *A61G 13/1295* (2013.01); *A61B 6/5258* (2013.01); *A61G 13/12* (2013.01); *G01N 23/06* (2013.01)

(58) Field of Classification Search
CPC ............... A61B 6/00; A61B 6/02; A61B 6/04; A61B 6/0407; A61B 6/0421; A61B 6/0428; A61B 6/0485; A61B 6/48; A61B 6/482; A61B 6/50; A61B 6/505; A61B 6/52; A61B 6/5211; A61B 6/5217; A61B 6/5252; G01N 23/00; G01N 23/02; G01N 23/06; G01N 23/08; G01N 23/083; G01N 23/087; A61G 13/00; A61G 13/10; A61G 13/12; A61G 13/1205; A61G 13/1235; A61G 13/1245; A61G 13/126; A61G 13/128; A61G 13/1295; A61G 2210/00; A61G 2210/50

See application file for complete search history.

(56) References Cited

U.S. PATENT DOCUMENTS

| | | | |
|---|---|---|---|
| 6,233,473 | B1 | 5/2001 | Shepherd |
| 7,036,169 | B2 | 5/2006 | Marshall |
| 7,426,930 | B1 | 9/2008 | Bailey |
| 8,100,839 | B2 | 1/2012 | Galkin |

(Continued)

*Primary Examiner* — Anastasia Midkiff
(74) *Attorney, Agent, or Firm* — Kriegsman & Kriegsman

(57) ABSTRACT

A system for detecting lymphedema comprising a dual energy x-ray absorptiometry system and one or more spacer pads disposed within a field of view of the dual energy x-ray absorptiometry system. The dual energy x-ray absorptiometry system comprises an x-ray source and a patient support platform, wherein the patient support platform is configured to receive a patient in a supine position with the x-ray source disposed above the patient support platform. The one or more spacer pads are configured to be positioned between body parts of the patient.

17 Claims, 2 Drawing Sheets

(56) References Cited

U.S. PATENT DOCUMENTS

| | | |
|---|---|---|
| 2005/0081865 A1 | 4/2005 | Hubert |
| 2008/0144914 A1* | 6/2008 | Wagner ................ A61B 6/0421 |
| | | 382/132 |
| 2009/0124936 A1 | 5/2009 | Branch |
| 2010/0249666 A1 | 9/2010 | Branch |
| 2012/0046540 A1 | 2/2012 | Branch |

* cited by examiner

1

PATIENT SUPPORT PADS FOR USE IN DETECTING LYMPHEDEMA THROUGH X-RAY SCANS

CROSS REFERENCE TO RELATED APPLICATION(S)

This application is a continuation of U.S. patent application Ser. No. 13/894,700, filed May 15, 2013, allowed, which claims priority to provisional U.S. Patent Application Ser. No. 61/648,742, titled "Apparatus and Method for Detecting Lymphedema Using X-Ray Scans," filed on May 18, 2012, the disclosure of which is herein incorporated by reference in its entirety.

BACKGROUND

1. Field of the Invention

The present invention relates to the detection of lymphedema using x-ray scans, e.g., with use of a dual-energy absoptiometry (DXA) system.

2. Background of the Art

For treatment of invasive breast cancer, surgeons generally remove some of the lymph nodes under a patient's arm during a lumpectomy or mastectomy. The reason for lymph node removal is twofold. Because the lymphatic system is a whole body system, lymph nodes may be intentionally removed in order to reduce the opportunity for spread of cancer cells throughout the body. In addition, lymph nodes may be unintentionally removed because they are interwoven with axilla breast tissue within the body; removal of breast tissue unavoidably results in removal of lymph nodes.

The removal of lymph nodes may cause a lymphatic obstruction which blocks the lymph vessels that drain fluid from tissues throughout the body and allow immune cells to travel where they are needed. A lymphatic obstruction may in turn cause lymphedema, i.e., swelling due to the blockage of the lymph passages. Lymphedema is a feared complication of cancer treatment and one that negatively impacts survivorship. Lymphedema is a chronic disease that usually requires lifelong management as it may result in complications such as chronic wounds and ulcers, skin breakdown and lymph-tissue types of cancers. Early detection of lymphedema may reduce the amount of swelling, discomfort and risk for a patient.

Whole body scanning is one approach to estimating body mass or assessing assorted body compositions, such as distribution of fat, lean mass, bone, and fat mass index. One problem with using a whole body scanning system to estimate body mass involves the delineation of body parts during the scan. In particular, when a patient lies in the supine position, there is a tendency for extra chest tissue, such as the patient's breasts, to fold over onto the arm. Similarly, if the patient's feet and legs are spaced too close together, there may be difficulties delineating the individual masses of the legs. Overlapping tissue during the scan can decrease the accuracy in body mass measurements for the individual body parts.

SUMMARY

What is needed, then, is an apparatus and/or method to assist in delineating body parts when a patient undergoes a body scan, e.g., using a DXA scanner. It is realized that the ability of an x-ray body scan to accurately and precisely measure body mass may be leveraged for early diagnosis of lymphedema, thereby enabling early treatment and helping to reduce complications associated with the disease. Early signs of lymphedema may be detected through an increase in body mass resulting from the accumulation of fluid in patient's appendages. Because x-ray scanning provides accurate measurement of body mass, an easy and reliable method for early detection of lymphedema is provided.

According to one aspect, the invention relates to a system for detecting lymphedema comprising a dual energy x-ray absorptiometry system comprising an x-ray source and a patient support platform. The patient support platform is configured to receive a patient in a supine position with the x-ray source disposed above the patient support platform. The system also comprises one or more spacer pads disposed with a field of view of the dual energy x-ray absorptiometry system, the one or more spacer pads configured to be positioned body parts of the patient.

The foregoing aspect can include any one or more of the following embodiments. The one or more spacer pads can comprise low x-ray attenuation material. The low x-ray attenuation material can be radiographic foam. Each of the one or more spacer pads can be uniformly constructed. The system can further comprise a sanitary cover to cover each of the one or more spacer pads, the sanitary cover made of clear material. A height of each of the one or more spacer pads can exceed a maximum body thickness of the patient. The one or more spacer pads can be rigid so that the one or more spacer pads does not flex during use. The one or more spacer pads can be low weight. The one or more spacer pads can be positioned between at least one of an arm and trunk of the patient or legs of the patient.

In another aspect, the invention relates to a method of detecting lymphedema comprising providing a dual energy x-ray absorptiometry system, the system comprising an x-ray source and a patient support platform, positioning a patient in a supine position on the patient support platform such that the patient is between the x-ray source and the patient support platform, and positioning a spacer pad between body parts of the patient such that the spacer pad is positioned within a field of view of the dual energy x-ray absorptiometry system.

This aspect can include any one or more of the following embodiments. The method can further comprise scanning the patient using the dual energy x-ray absorptiometry system to detect lymphedema. The spacer pad can comprise low x-ray attenuation material. The low x-ray attenuation material can be radiographic foam. The spacer pad can be uniformly constructed. The spacer pad can be covered by a sanitary cover, the sanitary cover made of clear material. A height of each of the one or more spacer pads can exceed a maximum body thickness of the patient. The spacer pad can be rigid so that the spacer pad does not flex during scanning. The spacer pad can be low weight. The spacer pad can be positioned between at least one of an arm and trunk of the patient or legs of the patient.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral.

For purposes of clarity, not every component may be labeled in every figure. In the figures.

DETAILED DESCRIPTION

Except as otherwise noted, the articles "a," "an," and "the" mean "one or more."

Figure 1:
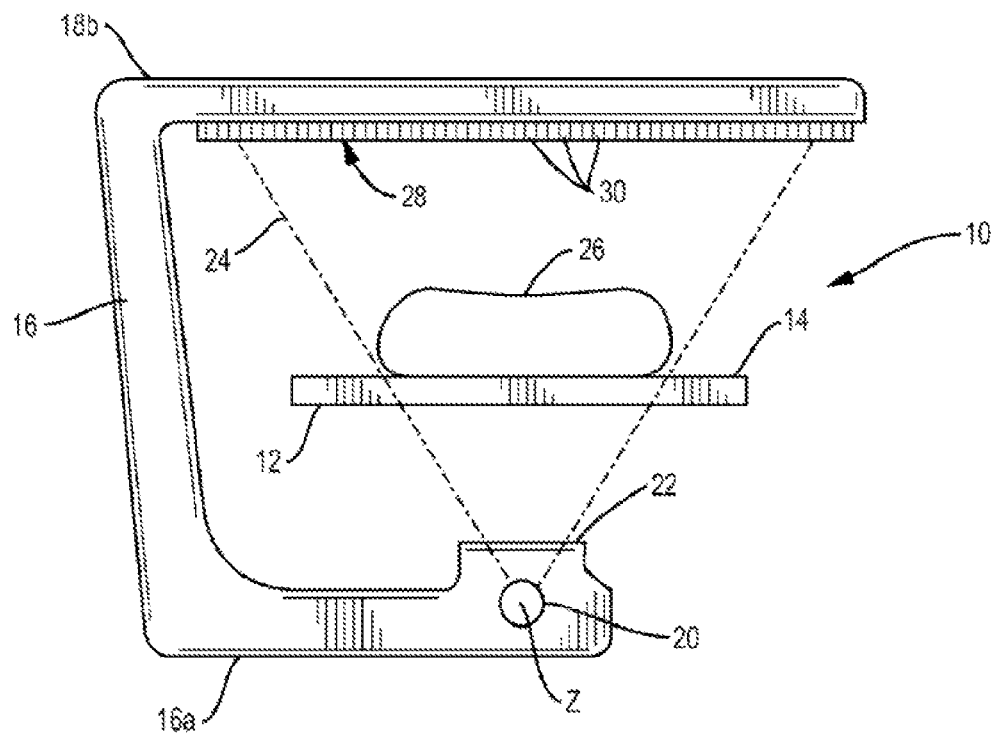
FIG. 1 is a simplified and schematic cross-sectional elevation illustrating a fan-shaped distribution of x-rays in a DXA system in which lymphedema can be detected.

FIG. 1 illustrates a DXA system 10. The DXA system 10 includes a patient table 12 having a support surface 14 that can be considered horizontal and planar in this simplified explanation and illustration, which is not necessarily accurate in scale or geometry and which is used here solely to illustrate and explain certain principles of operation. A human patient 26 is supine on surface 14. The length of the patient is along a horizontal longitudinal axis defined as the y-axis and the patient's arms are spaced from each other along the x-axis. A C-arm 16 has portions 16a and 18b extending below and above table 10, respectively, and is mounted in a suitable structure (not shown expressly) for moving at least parallel to the y-axis along the length of patient 26. Lower portion 16a of the C-arm carries an x-ray source 20 that can emit x-rays limited by an aperture 22 into a fan-shaped distribution 24 conforming to a plane perpendicular to the y-axis. The energy range of the x-rays can be relatively wide, to allow for the known DXA dual-energy x-ray measurements, or can be filtered or generated in a narrower range to allow for single energy x-ray measurements. The x-ray distribution can be continuous within the angle thereof or can be made up, or considered to be made up, of individual narrower beams. The x-ray distribution 24 can encompass the entire width of the patient as illustrated, or it can have a narrower angle so the entire patient can be covered only by several passes along the y-axis and the x-ray measurements from the several passes can be combined as is known in the art to simulate the use of a wider fan beam, as typical in current commercial DXA systems. Alternatively, a single, pencil-like beam of x-rays can be used to scan selected regions of the patient's body, e.g. in a raster pattern. The x-rays impinge on x-ray detector 28, which can comprise one or more linear arrays of individual x-ray elements 30, each linear array extending in the x-direction, or a continuous detector where measurements for different positions along the detector can be defined in some manner known in the art, or can be another form of detector of x-rays. C-arm 16 can move at least along the y-axis, or can be maintained at any desired position along that axis. For any one position, or any one unit of incremental travel in the y-direction of arm 16, detector 28 can produce one or several lines of raw x-ray data. Each line can correspond to a row of pixels in a resulting image, which row extends in a direction corresponding to the x-direction. Each line corresponds to a particular position, or range of positions, of the C-arm in its movement along the y-axis and/or a particular linear detector, and comprises a number of individual measurements, each for a respective detector element position in the line, i.e., represents attenuation that the x-rays have suffered in traveling from source 20 to a respective detector element position over a specified time interval. A DXA system takes a higher x-ray energy measurement H and a lower x-ray energy measurement L from each detector element position, and carries out initial processing known in the art to derive, from the raw x-ray data, a set of pixel values for a projection image. Each pixel value comprises a high energy value H and a low energy value L. This can be achieved by rapidly alternating the energy level of the x-rays from source 20 between a higher and a lower range of x-ray energies, for example by rapidly rotating or otherwise moving a suitable filter in or out of the x-rays before they reach patient 26, or by controlling the x-ray tube output, and/or by using an x-ray detector 28 that can discriminate between energy ranges to produce H and L measurements for each pixel position, e.g., by having a low energy and a high energy detector element side-by-side or on top of each other for respective positions in the detector array. The H and L x-ray measurements for the respective pixel positions are computer-processed as known in the art to derive estimates of various parameters, including, if desired, body composition (total mass, fat mass, and lean mass). Nonlimiting examples of DXA systems include those described in U.S. Patent Application Publication Nos. 2011/0235886 and 2011/0311122.

Figure 2:
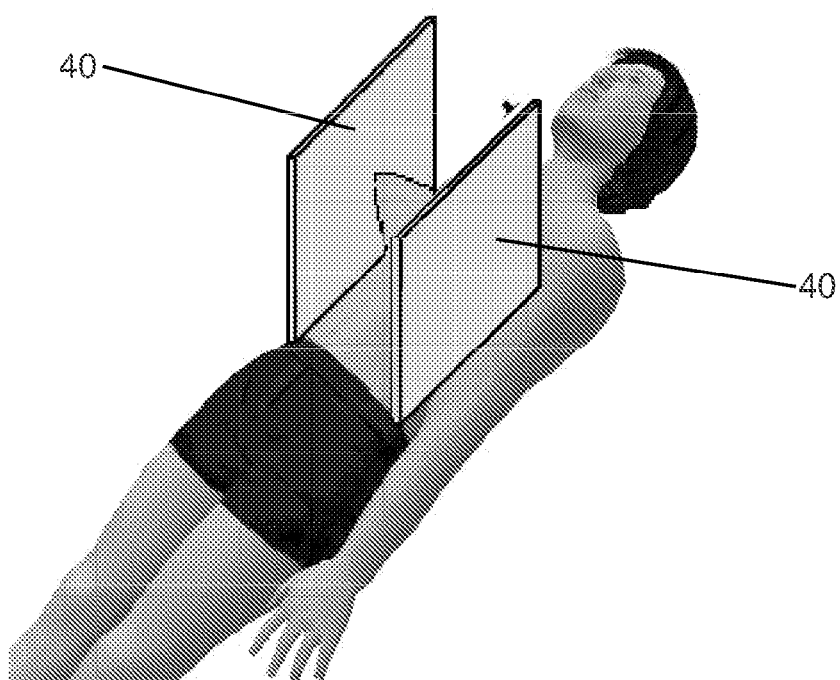
FIG. 2 illustrates a simplified and schematic perspective view of a patient with spacer pads according to an embodiment of the present invention.
Figure 4:
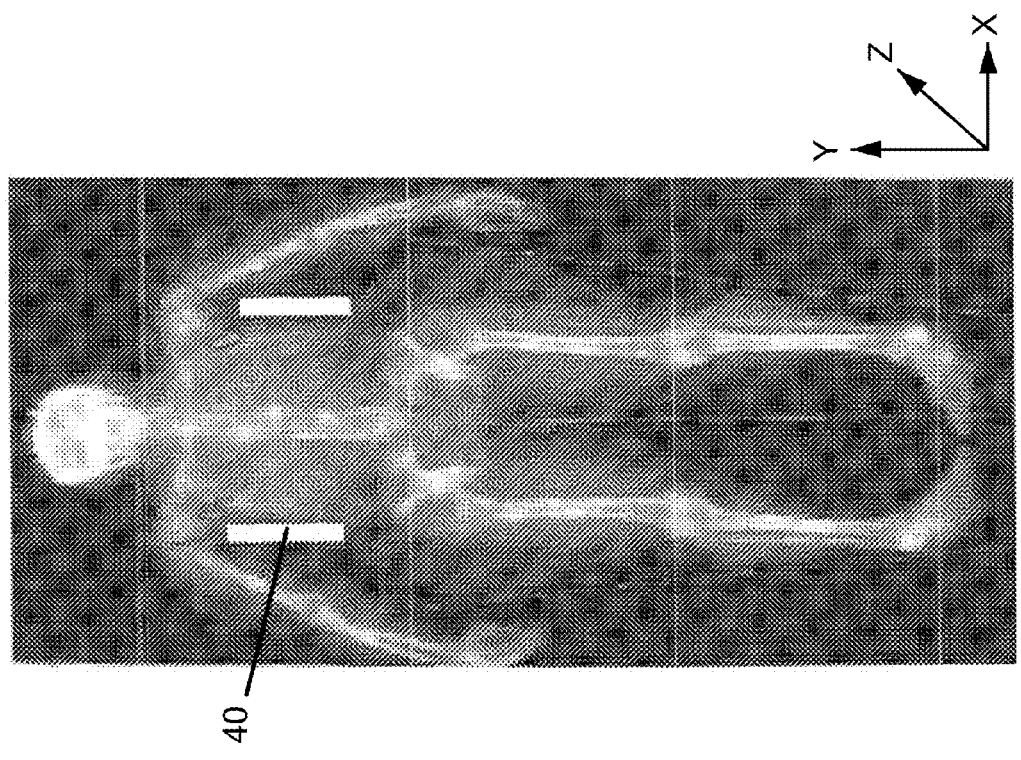
FIG. 4 illustrates a projection image of a patient with spacer pads taken with a DXA system.
Figure 3:
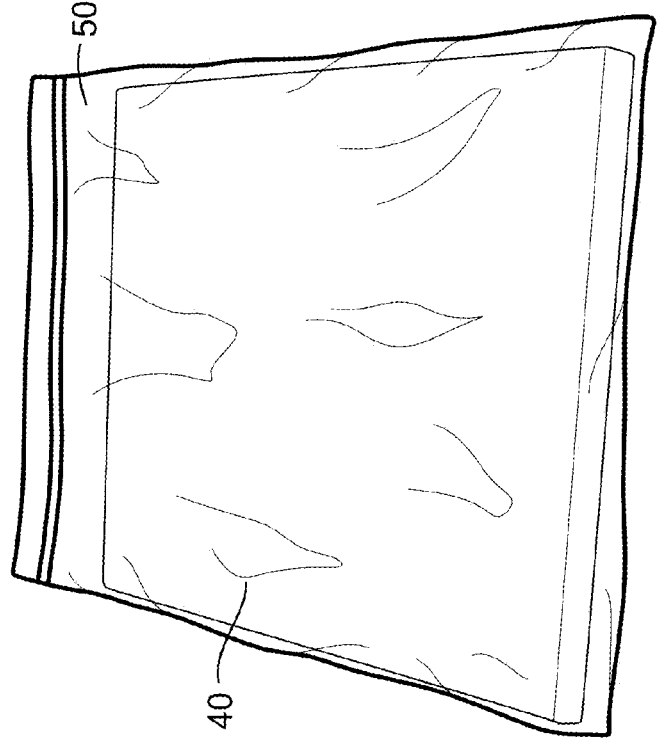
FIG. 3 illustrates a schematic perspective view of a spacer pad in accordance with an embodiment of the present invention.

FIG. 2 illustrates spacing pads of such construction in use to space the arms of a patient from the torso. As the patient is prepared for the image scan, each pad is placed between an arm and trunk of the patient, as high up into the armpit of the patient as is comfortable. Hands may be positioned vertically, but not against the hips to enable visualization of the arms cleanly cut from the trunk for analysis. Although not illustrated, it is appreciated that a spacer pad may also be positioned between the legs of the patient. FIG. 4 illustrates an exemplary scan which has been obtained using the spacing pads, and illustrating the clear delineation provided using the invention. FIG. 3 illustrates an exemplary pad of the invention, encased for use in a sanitary, disposable plastic bag.

Such an arrangement enables the clear delineation of the individual body parts of a patient, allowing for more accurate mass determinations for various body parts and facilitating the comparison of different masses between related appendages. As a result, lymphedema may be more rapidly identified and a patient may receive treatment before appreciable progression of the chronic disease.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

All parts, ratios, and percentages herein, in the Detailed Description and Claims are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All documents cited herein are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. A system for analyzing a body composition of a patient comprising:
    a dual energy x-ray absorptiometry system comprising a computer, an x-ray source and a patient support platform, wherein the patient support platform is configured to receive the patient in a supine position and wherein the dual energy x-ray absorptiometry system is configured to scan the patient to measure the body composition; and
    one or more spacer pads disposed within a field of view of the dual energy x-ray absorptiometry system, the one or more spacer pads configured to be positioned between body parts of the patient;
    wherein the computer processes image information acquired with the dual energy x-ray absorptiometry system and detects the one or more spacer pads to provide an analysis of the body composition, such that the analysis of the body composition does not include information about the one or more spacer pads.

2. The system of claim 1, wherein the one or more spacer pads comprises low x-ray attenuation material.

3. The system of claim 2, wherein the low x-ray attenuation material is radiographic foam.

4. The system of claim 1, wherein each of the one or more spacer pads is uniformly constructed.

5. The system of claim 1 further comprising a sanitary cover to cover each of the one or more spacer pads, the sanitary cover made of clear material.

6. The system of claim 1, wherein a height of each of the one or more spacer pads exceeds a maximum body thickness of the patient.

7. The system of claim 1, wherein the one or more spacer pads is rigid so that the one or more spacer pads does not flex during use.

8. The system of claim 1, wherein the one or more spacer pads is positioned between at least one of an arm and torso of the patient and legs of the patient.

9. A method of analyzing a body composition of a patient comprising:
    providing a dual energy x-ray absorptiometry system, the system comprising a computer, an x-ray source and a patient support platform;
    positioning the patient in a supine position on the patient support platform;
    positioning a spacer pad between body parts of the patient such that the spacer pad is positioned within a field of view of the dual energy x-ray absorptiometry system;
    scanning the patient with the dual energy x-ray absorptiometry system to measure the body composition; and
    computer processing image information acquired from the scanning step and detecting the spacer pad to provide an analysis of the body composition, such that the analysis of the body composition does not include information about the spacer pad.

10. The method of claim 9 further comprising scanning the patient using the dual energy x-ray absorptiometry system to detect lymphedema.

11. The method of claim 9, wherein the spacer pad comprises low x-ray attenuation material.

12. The method of claim 11, wherein the low x-ray attenuation material is radiographic foam.

13. The method of claim 9, wherein the spacer pad is uniformly constructed.

14. The method of claim 9, wherein the spacer pad is covered by a sanitary cover, the sanitary cover made of clear material.

15. The method of claim 9, wherein a height of each of the one or more spacer pads exceeds a maximum body thickness of the patient.

16. The method of claim 9, wherein the spacer pad is rigid so that the spacer pad does not flex during scanning.

17. The method of claim 9, wherein the spacer pad is positioned between at least one of an arm and torso of the patient or legs of the patient.

* * * * *